United States Patent [19]

Condra et al.

[11] Patent Number: 5,436,131
[45] Date of Patent: Jul. 25, 1995

[54] COLOR SCREENING ASSAY FOR IDENTIFYING INHIBITOR RESISTANT HIV PROTEASE MUTANTS

[75] Inventors: Jon H. Condra, Abington; Donald J. Graham, Green Lane; Leah Gotlib, Wynnewood, all of Pa.

[73] Assignee: Merck & Co., Inc., Rahway, N.J.

[21] Appl. No.: 45,264

[22] Filed: Apr. 2, 1993

[51] Int. Cl.[6] ............................................... C12Q 1/37
[52] U.S. Cl. ........................... 435/7.4; 435/320.1; 435/219; 435/23; 435/24
[58] Field of Search ............... 435/7.4, 6, 320.1, 219, 435/7.6, 23, 24; 436/164

[56] References Cited

FOREIGN PATENT DOCUMENTS 0421109  10/1991  European Pat. Off. .

OTHER PUBLICATIONS

DBA Abstract, Accession No. 90-03222, Wolf, German Patent No. De 3,819,846.

Kohl et al., Proc. Natl. Acad. Sci. USA, vol. 85, (Jul. 1988), pp. 4686–4690.

*Primary Examiner*—Margaret Parr
*Assistant Examiner*—Scott W. Houtteman
*Attorney, Agent, or Firm*—Roy D. Meredith; Charles M. Caruso

[57] ABSTRACT

A chromogenic assay is described for the identification and isolation of drug-resistant HIV protease mutants. Coversely, the assay is useful to screen for new inhibitors of HIV protease, e.g., inhibitors not affected by drug-resistance of the HIV protease. This color screening assay contains a vector comprising a regulatable promoter which controls the transcription of two adjacent structural sequences, one sequence coding for HIV protease or mutant thereof, the other sequence coding for beta-galactosidase with an amino acid substrate insert cleavable by HIV protease. A library of HIV proteases is also described and is isolated in the form of a collection of such vectors, which is a color screen vector library.

1 Claim, 1 Drawing Sheet

FIG.1

COLOR SCREENING ASSAY FOR IDENTIFYING INHIBITOR RESISTANT HIV PROTEASE MUTANTS

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E., et. al., Proc. Natl. Acad. Sci. USA, 85, 4686 (1988), demonstrated that genetic inactivation of the HIV encoded protease resulted in the production of immature, non-infectious virus particles. These results suggest that inhibition of the HIV protease represents a viable method for the treatment of AIDS and the prevention or treatment of infection by HIV.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)]. Applicants construct a vector and expression system for HIV protease. Related an includes Baum, E. Z. et al., Proc. Natl. Acad. Sci. 87, 10023 (1990).

The particular advantages of the present invention include the coordinate expression of functional HIV protease and a reporter beta-galactosidase having an insert cleavable by the HIV protease. The coordinate expression results from the transcription of a single dicistronic mRNA. Control over the expression of enzyme (HIV protease) and substrate (the cleavable insert) is readily achieved with this type of recombinant construction.

Further, the present invention is directed to a rapid method of identifying drug-resistant HIV protease mutants. Because only the HindIII site on the 5' side of the β-galactosidase gene is reconstructed in the cloning, the HIV protease gene is flanked by unique NdeI and HindIII sites, enabling easy removal and insertion of alternate protease genes. Thus, libraries of mutagenized protease genes for screening are constructed and inserted into this vector as NdeI-HindIII fragments.

Finally, because the promoter controlling the coordinate expression is itself regulatable, manipulation of the internal concentration of HIV protease is achieved. This arrangement avoids the toxic effects of intracellular HIV protease. Applicants induce the regulatable promoter, here the tryptophan promoter, only when further growth of the host cell E.coli is no longer needed.

BRIEF DESCRIPTION OF THE INVENTION

A chromogenic assay is described for the identification and isolation of drug-resistant HIV protease mutants. Conversely, the assay is useful to screen for new inhibitors of HIV protease, e.g., inhibitors not affected by drug-resistance of the HIV protease. This color screening assay contains a vector comprising a regulatable promoter which controls the transcription of two adjacent structural sequences, one sequence coding for HIV protease or mutant thereof, the other sequence coding for beta-galactosidase with an amino acid substrate insert cleavable by HIV protease. A library of HIV proteases is also described and is isolated in the form of a collection of such vectors, which is a color screen vector library.

DETAILED DESCRIPTION OF THE INVENTION

Applicants have constructed a color screen vector useful for assaying HIV protease inhibitors, for constructing a library of expressed HIV protease mutants, and for detecting and isolating mutants of HIV protease that are resistant to HIV protease inhibitors. The vector contains two structural sequences that are coordinately transcribed into a dicistronic mRNA from the same promoter. The first sequence to be transcribed is HIV protease, the second sequence is a reporter protein that contains a substrate site cleavable by the HIV protease.

Since the vector contains a reporter gene which is assayed by the appearance of a chromogenic substrate, it is a color screen vector. In this invention, beta-galactosidase is inserted into the vector. This enzyme acts on 5-bromo-4-chloro-3-indolyl-beta-D-galactopyranoside to produce a blue product readily observeable by the eye.

A cleavable reporter provides a measure of the amount of cleaving enzyme, in this case HIV protease inhibitor. Beta-galactosidase is constructed with an oligopeptide insert containing the substrate site for HIV protease. This substrate sequence is as follows:

Glu Val Ser Phe Asn Phe Pro Gln Ile Thr (SEQ. ID. NO.: 14). The oligopeptide insert does not materially affect the enzymatic activity of beta-galactosidase, but once it is cleaved the beta-galactosidase is inactive.

Thus, in the presence of HIV protease inhibitor, bacterial colonies containing the color screen vector of this invention are blue in a suitable host such as E. coli. They are normally of white color due to the activity of the expressed HIV protease. If the vector contains a drug-resistant HIV protease mutant instead of its more active original NY5 HIV protease, the colonies will be a lighter blue.

Figure 1:
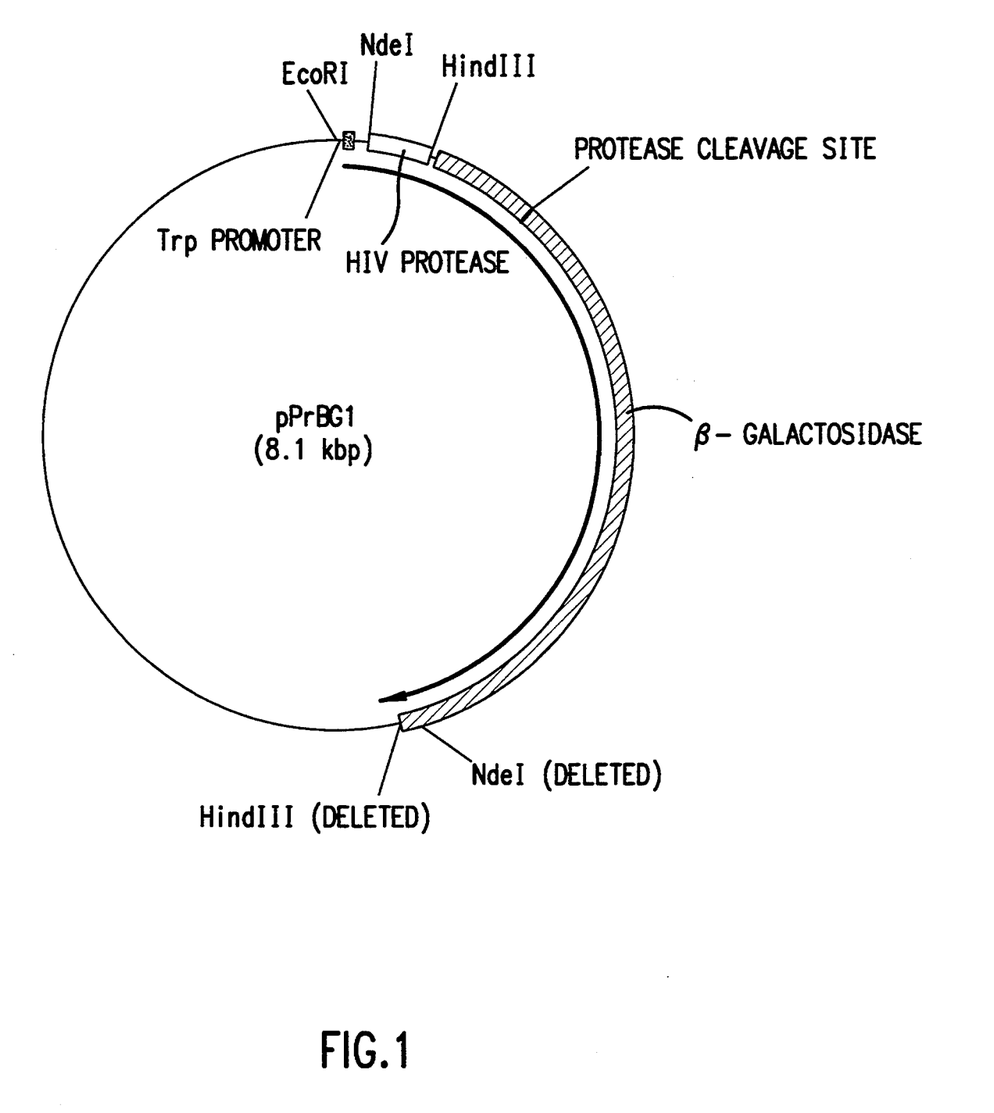
FIG. 1: Map of pPrBG1, an example of the color screen vector of the present invention.

The present invention is suitably embodied in pPrBG1, as set forth in FIG. 1. The trp promoter operatively expresses or transcribes a dicistronic mRNA, indicated by the inner arrow. This nRNA or message codes for the HIV protease and, downstream, a beta-galactosidase having inserted thereto an oligopeptide site cleavable by HIV protease.

The unique NdeI and HindIII sites at the ends of the HIV protease sequence provide a readily available and convenient site for insertion of a library of mutagenized HIV protease sequences. Thus the original HIV protease sequence can be mutagenized, then trimmed by digestion with NdeI and HindIII. The resulting heterogeneous collection of sequences with uniform ends is readily ligated with pPrBG1 digested with NdeI and HindIII, to form a color screen library of HIV protease mutants. Screening the resulting library for lighter blue colonies in the presence of the inhibitor will yield drug-resistant HIV protease mutants.

A. Preparation and Sequencing of DNA

Following well known and conventional practice, coding sequences are prepared by ligation of other sequences, restriction endonuclease digestion, cloning, mutagenesis, organic synthesis, or combinations thereof, in accordance with the principles and practice of constructing DNA sequences. For sequencing DNA, e.g., verification of a construct at the end of a series of steps, dideoxy DNA sequencing is the preferred method. Other DNA sequencing methods are well known.

Many treatises on recombinant methods have been published, including J. Sambrook et al., Molecular Cloning: A Laboratory Manual 2d Ed. 1978; L. G. Davis et al., Basic Methods in Molecular Biology Elsevier 1986; F. M. Ausubel, et al. (eds.), Current Protocols in Molecular Biology, Wiley Interscience 1988 (looseleaf).

Phosphoramidite chemistry in solid phase is the preferred method for the organic synthesis of oligodeoxynucleotides and polydeoxynucleotides. Many other organic synthetic methods are available and are readily adapted to the particular sequences of this invention by a person skilled in the art.

Amplification of DNA is a common step in the constructions of this invention, and is typically performed by the polymerase chain reaction (PCR). See, e.g., Mullins et al., U.S. Pat. No. 4,800,159 and other published sources. The basic principle of PCR is the exponential replication of a DNA sequence by successive cycles of primer extension. The extension product of one primer, when hybridized to another primer, becomes a template for the synthesis of another nucleic acid molecule. The primer template complexes act as substrate for DNA polymerase which, in performing its replication function, extends the primers. The region in common with both primer extensions, upon denaturation, serves as template for a repeated primer extension. The conventional enzyme for PCR applications is the thermostable DNA polymerase isolated from *Thermus aquaticus*, or Taq DNA polymerase. Numerous variations in the PCR protocol exist, and a particular procedure of choice in any given step in the constructions of this invention is readily performed by a skilled artisan.

B. Construction of HIV protease sequences, and expression vector.

Applicants have arbitrarily selected the particular protease sequence of the NY5 strain of HIV-1 to construct a structural sequence for a procaryotic expression vector. Virtually any other HIV-1 protease sequence can effectively substitute for that of the NY5 strain, provided that the substituted strain is not derived from a patient treated with an HIV protease inhibitor. The constructed sequence need not be the same as the original, or its complementary sequence, but instead may be any sequence determined by the degeneracy of the DNA code. Conservative amino acid substitutions may also be employed, or other minor modifications, such as an amino terminal methionine used herein.

A ribosome binding site active in the host expression system is ligated to the 5′ end of the HIV protease sequence, giving a synthetic gene. For convenience, applicants have ligated the *E.coli* ribosome binding site, and inserted a unique NdeI site overlapping the initiation codon ATG. At or near the 3′ end is a unique HindIII site.

An important feature in the construction of the HIV protease expression vector of this invention is the unique restriction endonuclease sites at or near each end of the HIV protease sequence. This feature allows for convenient and rapid substitution of mutagenized HIV protease sequences for subsequent screening of drug-resistant HIV protease mutants.

A large variety of hosts are now readily available for recombinant expression systems. A regulatable promoter is the most suitable for the present invention. For convenience, applicants have chosen to express the HIV protease under the control of the *E.coli* trp promoter. Other suitable regulatable promoters include lac, tac, recA, T7, $\lambda P_R$, or $\lambda P_L$.

The synthetic gene is then ligated to appropriately linearized plasmid, e.g., pTRP which is digested with ClaI and HindIII. The resulting plasmid, called pSyn7, expresses amino acids 1–99 of the NY5 strain of HIV-1 protease, and is preceded by the initiator methionine under the control of the *E.coli* trp promoter.

C. The Beta-galactosidase Sequence with an Insert Cleavable by HIV Protease

The reporter gene beta-galactosidase converts the chromogenic substrate 5-bromo-4-chloro-3-indolyl-beta-D-galactopyranoside (XGal) into a blue colored product. At certain sites in the primary sequence of beta-galactosidase, small oligopeptides can be inserted without inactivating the enzymatic activity. One such site is amino acid 79 of beta-galactosidase, see, e.g., Baum, E. Z. et al, supra. A vector coding for a readily assayable beta-galactosidase is selected. this case, applicants choose pCH110 (Phannacia), and cut it at the indicated site with SauI. A DNA duplex coding, when in frame, the following HIV protease substrate sequence is ligated into pCH110 linearized with SauI:

Glu Val Ser Phe Asn Phe Pro Gln Ile Thr Leu Glu (SEQ. ID. NO.: 14). Applicants use Oligonucleotides 1 and 2 (SEQ. ID. NO.:1 and SEQ. ID. NO.: 2, respectively, see Example 2) for such insertion and ligation into the DNA sequence corresponding to position 80 of the beta-galactosidase amino acid sequence, to afford a recombinant beta-gal plasmid.

It will be understood that a variety of other oligonucleotides may be used with like effect. For example, degenerate DNA fragments may be employed, or DNA sequences coding for alternative substrate sites for HIV protease, including those readily determined by conservative amino acid substitution. Organic synthesis with a gene machine is a convenient way of making these oligonucleotides for insertion and ligation.

Suitable alterative substrate sites for HIV protease include the following:

| | | |
|---|---|---|
| p17/p24: | Ser Gln Asn Tyr Pro Ile Val Gln | (SEQ. ID. NO.: 15) |
| p24/X: | Ala Arg Val Leu Ala Glu Ala Met | (SEQ. ID. NO.: 16) |
| X/p7: | Ala Thr Ile Met Met Gln Arg Gly | (SEQ. ID. |

| | | -continued | |
|---|---|---|---|
| p7/p6: | Pro Gly Asn Phe Leu Gln Ser Arg | (SEQ. ID. NO.: 17) (SEQ. ID. NO.: 18) |
| p6/PR: | Ser Phe Asn Phe Pro Gln Ile Thr | (SEQ. ID. NO.: 19) |
| PR/RT: | Thr Leu Asn Phe Pro Ile Ser Pro | (SEQ. ID. NO.: 20) |
| RT51/RNaseH: | Ala Glu Thr Phe Tyr Val Asp Gly | (SEQ. ID. NO.: 21) |
| RT/IN: | Arg Lys Ile Leu Phe Leu Asp Gly | (SEQ. ID. NO.: 22) |
| DEG1: | Gln Ile Thr Leu Trp Gln Arg Pro | (SEQ. ID. NO.: 23) |
| DEG2: | Asp Thr Val Leu Glu Glu Met Ser | (SEQ. ID. NO.: 24) |
| DEG3: | Asp Gln Ile Leu Ile Glu Ile Cys | (SEQ. ID. NO.: 25) | see, e.g., Debouk, C., AIDS Res. and Human Retroviruses 8, 153 (1992). Substrate sites typically add a two amino acid flanker on each side, e.g., sequences 14 and 19.

Further conventional steps include transformation and cloning in a host E.coli cell, e.g., SCSI cells (Stratagene). Transformants can be picked with a positively selectable marker, in this case ampicillin resistance. Using radioactively labeled oligonucleotide probe, colonies bearing the desired insert are identified and picked for cloning. Proper insertion of the oligodeoxynucleotide cassette coding for the HIV protease substrate site (SEQ. ID. NO.: 14) is verified by dideoxy sequencing using a primer coding for a sequence upstream or downstream of such insertion, e.g., Oligonucleotide 3 (SEQ-.ID.NO.: 3).

The resulting recombinant beta-gal plasmid contains a modified beta-galactosidase which is a beta-galactosidase sequence with an insert cleavable by HIV protease.

D. Coordinate Expression Vector, e.g., pPrBG1

The modified beta-galactosidase is recovered from the recombinant beta-gal plasmid of Section C, above, by PCR amplification with oligonucleotide primers that insert a 5' ribosome binding site and two 3' stop codons. See, for example, oligonucleotides 4 and 5 (SEQ ID NO.: 4 and 5, respectively). The resulting PCR product is trimmed by appropriate restriction endonucleases, in one instance illustrated as the digestion with BsaI and HindIII to give a PCR product which is the modified beta-galactosidase having HindIII-compatible termini.

The expression vector for HIV protease, e.g., pSyn7 in Section B above, is digested with an appropriate restriction endonuclease. For pSyn7, the endonuclease HindIH is used. Treatment with an alkaline phosphatase, such as calf intestinal alkaline phophatase, removes unwanted terminal phosphates. There follows a ligation reaction of (1) the modified beta-galactosidase having HindIII-compatible termini, and (2) pSyn7 linearized with HindIII.

Further conventional steps include transformation and cloning in a host E.coli cell, e.g., SCS1 cells (Stratagene). Transformants can be picked with a positively selectable marker, in this case ampicillin resistance. Using radioactively labeled oligonucleotide probe, colonies bearing the desired insert are identified and picked for cloning. Proper insertion of the oligodeoxynucleotides cassette coding for the modified beta-galactosidase having HindIII-compatible termini is verified by dideoxy sequencing using the appropriate primer. Applicants picked oligonucleotides 6 and 7 (SEQ. ID. NO.: 6 and 7, respectively) for verification.

The resulting plasmid has two NdeI sites, one at or near the 5' terminus of the HIV protease insert, the other near the 3' end of the modified beta-galactosidase. Removal of the latter NdeI site is necessary, so that new HIV protease genes can be substituted conveniently. By gapped-duplex oligonucleotide mutagenesis with the appropriate primer (herein oligonucleotide 8, which is SEQ. ID. NO.: 8) the unwanted restriction site is removed. Removal is verified by colony hybridization with radioactively labeled oligonucleotide 8 and/or restriction mapping.

The resulting plasmid is pPrBG1, as mapped in FIG. 1. This plasmid coordinately expresses a functional HIV protease and a reporter beta-galactosidase having an insert cleavable by the HIV protease. The HIV protease sequence is flanked by unique NdeI and HindlII sites.

E. DNA Libraries of Mutagenized HIV Protease Genes

Mutagenesis in vitro of the gene for the functional HIV protease is readily accomplished by contacting the DNA with any one or more of a variety of mutagens, or by other means. The available methods include the following: generation of nested sets of deletion mutants (restriction digestion and Bal 31 treatment); linker-scanning mutagenesis; oligonucleotide-directed mutagenesis; the Kunkel method of oligonucleotide-mediated mutagenesis by selection against template strands containing uracil; insertion of linkers; insertion of linkers formed from degenerate pools of mutagenized oligonucleotides; treatment of double-stranded DNA with mutagens; treatment of single-stranded DNA with mutagens; misincorporation of nucleotides by DNA polymerase; and organic synthesis and assembly of target sequences with mutually priming long oligonucleotides The success in chemical mutagenesis depends on whether the target DNA is single-stranded or double-stranded, the nature of the chemical mutagen, its concentration, time of exposure, and the like. It is advantageous to have a screening system for the resulting library of mutants. For a general discussion of in vitro mutagenesis methods adaptable for the purposes of constructing the particular DNA libraries of the present invention, see, e.g., J. Sambrook, supra, chapter 15; and F. M. Ausubel, supra, chapter 8.

One preferred method of mutagenesis is contacting the target DNA in single-stranded form, then sequencing and/or cloning. For this purpose, the small icosahedral or filamentous single-stranded DNA bacteriophages, such as X174 or f1 (fd, M13), are well characterized and make ideal vectors.

Both the positive and negative strands of the HIV protease gene to be mutagenized are cloned, then subjected to limited contact with one or more mutagens. Mutagens useful for treating single-stranded DNA include, but are not limited to:
sodium bisulfite,
nitrous acid,
formic acid, and
hydrazine.

Limited contact with any of these mutagens avoids multiple nucleotide substitutions on each strand, and this can be readily accomplished by titration of the chemical mutagen, including its concentration, reaction time, and temperature.

After removal of the mutagens, the single-stranded circular DNA is rendered double-stranded and trimmed for convenient insertion and expression. A universal sequencing primer and avian reverse transcriptase are preferred for polymerization. Double-stranded products are digested with NdeI and HindIII, and purified by agarose gel electrophoresis. Ligation into linearized pPrBG1 or other appropriate coordinate expression vector creates a color screen vector library of mutagenized HIV protease genes suitable for screening.

F. Color Screening Assay

The principle of the procedure is to replica plate a master plate of transformed colonies, then treat the replica plate with promoter inducer, HIV protease inhibitor and chromogenic substrate. The lighter colored colonies from the plate treated with inhibitor and substrate are identified. Keying back from this treated plate to the master plate (or other untreated plate) localizes the desired colony, i.e., a transformant that expresses a drug-resistant HIV protease.

Typically, a master plate is prepared by merely plating out transformants of a suitable recipient strain bearing the color screen vector library of mutagenized HIV protease genes. For most applications, the master plate is an agar dish containing growth media suitable for the recipient strain. In some instances, the master plate may be a nitrocellulose disk which itself is a replica of a pattern of colonies on an agar dish, or, instead, it may be a replica of a pattern of colonies on another nitrocellulose disk.

A suitable recipient is readily picked for the color screen vector library. For convenience, applicants have picked $E.coli\ K$-12 strain LS743. An essential charateristic of a suitable recipient and the color screen vector library is a system for positively selecting only transformed clones, e.g., applicants eliminate untransformed colonies by incubating in the presence of an antibiotic such as ampicillin. An additional advantageous characteristic is the facilitative uptake of hydrophobic drug entities (such as HIV protease inhibitor), here embodied in envA). It will be understood that selecting and obtaining an appropriate recipient cell strain is within the skill of the art.

The master plate having been prepared, it is replica plated onto a membrane filter or other matrix to give a colony lift. Nitrocellulose is the preferred membrane filter, but nylon is a feasible substitute. A large number of master plates with a corresponding number of colony lifts may be prepared, depending on the size of the color screen vector library and the desired amount of screening.

The resulting colony lifts are treated with a selected HIV protease inhibitor, e.g., L-689,502, the structure and synthesis of which is disclosed in Thompson, W. J. et al., J.Med. Chem. 35, 1685 (1992). A wide variety of other HIV protease inhibitors are useful in this assay.

There are numerous patent and literature publications disclosing the synthesis and characterization of other inhibitors of HIV protease. The reaction conditions suitable for a given inhibitor in the treatment of the colony lifts are readily determined by a skilled artisan.

Once the colony lifts are treated with inhibitor, they are developed by inducing the expression of the reporter enzyme in the presence of a chromogenic substrate, to give induced colony lifts. To do this, treated colony lifts are simply transferred physically to induction plates. For convenience, applicants prepare the induction plates as a solid agar containing growth media, with inducing agent (beta-indoleacrylic acid), antibiotic (ampicillin to maintain plasmid selection), chromogenic substrate (5-bromo-4-chloro-3-indolyl-beta-D-galactopyranoside) and HIV protease inhibitor. The appropriate choice of inducing agent, antibiotic, and chromogenic substrate will depend on the vector library construction, the promoter for coordinate expression, and the reporter; and their selection is within the skill of the art.

The induced colony lifts show a pattern of blue colored colonies, with a few lighter blue. The location and plate number of the the lighter blue colonies is noted and used to refer back to the master plate to pick the same colony. Any colonies exhibiting a lighter color than wild type colonies are recovered from the master plate and regrown for DNA sequencing, repeated color screening, in vitro expression and characterization of drug resistance in the purified enzyme.

Conversely, the color screening assay is useful for screening new inhibitors of HIV protease. Colonies of a single cloned vector are grown, treated with a series of potentially inhibitory compounds to be assayed, then induced in the presence of chromogenic substrate. Blue colonies reveal the presence of an effective inhibitor, and such colonies are readily identified against white colonies containing active HIV protease without effective inhibitor.

EXAMPLE 1

Construction of pSyn7, a Vector for the Expression of HIV Protease Sequences

I. A synthetic gene coding for protease from the NY5 strain of HIV-1 is assembled from six oligonucleotides ranging in length from 105 to 125 bases. The gene contains, from the 5'-end, a ClaI site, 33 base pairs containing an E.coli ribosome binding site, a unique NdeI site overlapping the translational initiation codon (ATG), 297 base pairs encoding the 99 amino acids of the protease, a translational termination codon (TAA) and a HindHi site. This sequence (shown after digestion with ClaI and HindIII) is as follows:

```
           10         20         30         40         50        (SEQ ID. NO. 13)
        CGATAATGTA TGGATTAAAT AAGGAGGAAT AAGACATATG CCTCAGATCA 60         70         80         90        100
        CTCTGTGGCA GCGGCCGCTG GTTACTATCA AAATCGGTGG CCAGCTGAAA 110        120        130        140        150
        GAAGCTCTTC TAGACACTGG TGCTGACGAC ACTGTTCTCG AGGAAATGAA 160        170        180        190        200
        CCTGCCCGGG CGTTGGAAAC CTAAAATGAT CGGTGGTATC GGTGGTTTCA 210        220        230        240        250
        TCAAAGTTCG TCAGTATGAT CAGATCCTGA TCGAGATCTG CGGTCATAAA
```

```
       260        270          280        290        300
GCTATCGGTA CCGTTCTGGT TGGTCCTACT CCTGTTAACA TCATCGGTCG 310        320        330      339
TAACCTGCTG ACCCAGATCG GCTGCACTCT GAACTTCTA
```

Oligonucleotides are synthesized by the solid phase method on a DNA synthesizer using phosphoramidite chemistry, purified by electrophoresis through a 12% denaturing polyacrylamide gel and visualized by UV shadowing. Following excision of the bands containing the full length products, oligonucleotides are recovered from the acrylamide by soaking and desalted by dialysis against water.

Oligonucleotides are phosphorylated with polynucleotide kinase and complementary fragments are annealed and ligated in two consecutive reactions to ClaI/HindIII-digested pTRP (Darke, P. et al., J. Biol. Chem. 264, 2307 (1989))using conventional procedures (Sambrook J. et al., Molecular Cloning: A Laboratory Manual, 2nd Ed. Cold Spring Harbor 1989). The sequence of the entire synthetic gene was confirmed by dideoxy sequencing. The resulting plasmid, called pSyn7, expresses amino acids 1–99 of the protease preceded only by the initiator Met under the control of the E.coli trp promoter.

EXAMPLE 2

Insertion of an HIV Protease-cleavable site into the E.coli β-galactosidase gene A. Plasmid pCH110 (from Pharmacia) is linearized with SauI. The reaction is extracted with phenol and chloroform, then ethanol-precipitated. A duplex of the following synthetic oligodeoxyribonucleotides is ligated into this unique site.

Oligo 1: 5'-TGAGGTGAGCTTTAACTTCCCTCAGATCACTCT-3'  (SEQ. ID. NO.: 1)

Oligo 2: 5'-TCAAGAGTGATCTGAGGGAAGTTAAAGCTCACC-3'  (SEQ. ID. NO.: 2)

B. Competent E.coli SCS1 cells (Stratagene) are transformed with this ligation mix, and transformants are selected on LB agar containing 100 µg/ml ampicillin. Colonies bearing the desired insert are identified by colony hybridization with $^{32}$P-labeled Oligo-nucleotide 1 as probe, in 6X SSC/5X Denhardt's Solution/0.1% SDS at 65° C., followed by washing in 6X SSC at 65° C. Radioactive colonies are identified by autoradiography using X-ray film.

C. The desired recombinant plasmid is recovered from a hybridizing colony by growth overnight in LB broth containing 100 µg/ml ampicillin, and purified by alkaline lysis and ethidium bromide-CsCl centrifugation. Proper insertion of the oligonucleotide cassette is verified by dideoxy DNA sequencing using the following oligonucleotide primer:

Oligo 3: 5'-GCTTTGCCTGGTTTCCG-3'   (SEQ. ID. NO.: 3)

EXAMPLE 3

Cloning of cleavable β-galactosidase gene into HIV protease expression vector pSyn7 to give pPrBG1, a screening vector for drug-resistant HIV protease mutants A. The modified β-galactosidase gene is recovered from the plasmid of Example 2 by polymerase chain reaction amplification using the following primers:

Oligo 4: 5'-CGATCAAGCTTAAGCCGTAGATAAACAGGC-3'    (SEQ. ID. NO.: 4)

Oligo 5: 5'-ATCCTGGGTCTCGAGCTATTATTTTTGACACCAGACCAACTG-3'   (SEQ. ID. NO: 5)

The PCR amplification reaction is carried out for 25 cycles as follows:
1 min at 94° C.;
2 min at 37° C.;
3 min at 72° C.

This procedure inserts a ribosome binding site 5' of the β-galactosidase gene and two stop codons at its 3' end.

B. HindIII-compatible termini are generated in the PCR product by digestion with BsaI and HindIII.

C. Plasmid pSyn7 is digested with HindIII, then treated with calf intestinal alkaline phosphatase. A quantity of 0.05 µg of the digested PCR product of Step B are ligated to 0.1 µg HindIII-cut pSyn7 DNA in a final volume of 10 µl, using T4 DNA ligase, for 3 hr at 16° C.

D. Competent E.coli SCS1 (Stratagene) are transformed with this ligation mix, and transformants are selected on LB agar containing 100 µg/ml ampicillin. The desired recombinants are identified by colony hybridization with $^{32}$P-oligo 1 as described in Example 2, Part B.

E. Plasmids are recovered from hybridizing colonies by growth overnight in LB broth containing 100 µg/ml ampicillin, and purified by alkaline lysis and ethidium bromide-CsCl centrifugation.

F. Proper insertion of the insert is verified by dideoxy DNA sequencing using the following oligonucleotide primers:

(SEQ. ID. NO.: 6)
Oligo 6: 5'-TTTTCGCTCATGTGAAGT-3'

(SEQ. ID. NO.: 7)
Oligo 7: 5'-TGCGTTCTGATTTAATCTG-3'

G. Using the gapped-duplex oligonucleotide mutagenesis method (Colonno, R. et al., Proc. Natl. Acad. Sci. 85, 5449 (1988)), the NdeI site within the β-galactosidase gene is eliminated. The mutagenic oligonucleotide and hybridization probe for this site removal is the following:

Oligo 8:  (SEQ. ID. NO.: 8)
5'-GTTTCCACATGGGGATT-3'

Removal of the NdeI site is verified by colony hybridization with $^{32}$P-oligo 8 and by loss of the site in restriction mapping using NdeI.

H. The resultant plasmid, pPrBG1, is selected by growth on LB agar containing 100 μg/ml ampicillin, grown in liquid culture and purified by alkaline lysis and ethidium bromide-CsCl centrifugation as described above.

In pPrBG1, the cleavable β-galactosidase gene and its ribosome binding site are inserted immediately 3' of the expressed HIV protease gene, under the control of the tryptophan promoter of pSyn7. A diagram of this plasmid is shown in FIG. 1. The HIV protease and its cleavable β-galactosidase reporter are therefore coordinately expressed from a single dicistronic mRNA. Because only the HindIII site on the 5' side of the β-galactosidase gene is reconstructed in the cloning, the HIV protease gene is flanked by unique NdeI and HindIII sites, enabling easy removal and insertion of alternate protease genes. Thus, libraries of mutagenized protease genes for screening are constructed and inserted into this vector as NdeI-HindIII fragments.

EXAMPLE 4

In Vitro Mutagenesis of the HIV-1 Protease Gene and Construction of Mutant Libraries in pPrBG1

I. The synthetic protease gene from plasmid pSyn7 is recovered from the plasmid by PCR amplification using the following oligonucleotide primers:

Oligo 9: 5'-AGGAGGAATTCGACATATGCCTCAGATCAC-3' (SEQ. ID. NO.: 9)

Oligo 10: 5'-CAGCCAAGCTTAGAAGTTCAGAGTGCAGCC-3' (SEQ. ID. NO.: 10)

Amplification is carried out as described in Example 3, Step A. This amplification adds an EcoRI site to the 5' end of the protease gene, permitting subsequent cloning. The amplified product is digested with EcoRI and HindIII, purified by agarose gel electrophoresis, and cloned into the EcoRI and HindIII sites of phagemids pGEM-7ZF(−) (Promega), to yield pGEM-Pr (+) and pGEM-Pr (−), respectively.

II. Single-stranded DNA of phagemids pGEM-Pr (+) and pGEM-Pr (−) is prepared by superinfection with phage M13K07 (Promega).

III. The purified single-stranded DNAs are subjected to mutagenesis in vitro with nitrous acid, hydrazine, or formic acid as previously described (Myers et al., Science 229, 242 (1985)), made double stranded with AMV reverse transcriptase and the primers:

(SEQ. ID 5'-NDAAIJACGACTCACTATA-3',
for pGEM-Pr(+), or (SEQ. ID 5'-NOETIJAGGTGACACTATA-3',
for pGEM-Pr(−)

IV. The double stranded products of the pGEM-Pr (+) and pGEM-Pr (−) reactions are pooled and digested with NdeI and HindIII. The mutagenized protease genes are recovered by agarose gel purification and ligated into the gel-purified NdeI/HindIII digested vector fragment of pPrBG1, to generate a randomly-mutagenized library of HIV protease genes in the screening vector.

V. E.coli K-12 strain LS743 (leu, thr, galK, lacΔU169, envA, Tn10, rpsL), was used as the recipient strain for the transformation. Competent LS743 cells are prepared as previously described (Hanahan D., J. Mol. Biol. 166, 557 (1983)) and transformed by the mutagenized protease library, plating on LB agar containing 100 μg/ml ampicillin at 37° C. overnight.

EXAMPLE 5

Screening HIV-1 Protease Mutant Libraries for Drug-Resistant Mutants

Transformants are generated in LS743 and colonies are lifted onto 82 mm diameter BAS85 nitrocelluose disks (Schleicher & Schuell). The disks are removed from the plates and placed, colony-side-up, on 1 ml puddles consisting of: 860 μl 1M Tris-Cl pH 7.4/0.15M NaCl, 138 μl dimethylsulfoxide (DMSO), and 2 l of a 10 mM stock of protease inhibitor L-689,502 (Thompson, W. J. et al., J. Med. Chem. 35, 1685 (1992)) in DMSO. After incubating 25 minutes, the filters are transferred to induction plates.

The plates are prepared as follows:

A. To prepare medium, into a volume of 254 ml of H$_2$O is dissolved 1.8 g Na$_2$HPO$_4$, 0.9 g KH$_2$PO$_4$, 0.15 g NaCl, 0.3 g NH$_4$Cl, and 0.6 g Difco casamino acids. The pH is brought to 7.4 with a few drops of 10N NaOH. A quantity of 4.5 g of Bacto agar is added, and the media is autoclaved 20 minutes, then cooled to 55° C. The following are then added: 3 ml of 20% (w/v) glucose, 0.6 ml of 1M MgSO$_4$, 30 μl of 1M CaCl$_2$, 300 μl of 100 mg/ml ampicillin, 300 μl of 20 mg/ml β-indoleacrylic acid (in 100% ethanol), 300 μl of 40 mg/ml XGal (5-bromo-4-chloro-3-indolyl-β-D-galactopyranoside (Boehringer-Mannheim)) in dimethylformamide, and 42 ml of DMSO. A volume of 20 ml of molten medium containing 78.4 μl of a 5.10 mM stock of drug is poured per plate. The medium is allowed to solidify, and the plates are used immediately for the assay.

A. The original master plates from the transformation are re-incubated at 37° C. until colonies are visible. These are stored at 4° C. as sources of viable cells for mutant characterizations.

II. The filters are incubated on the induction plates for 24 hours at 37° C. The resulting color of drug resistant colonies is a significantly lighter blue than drug sensitive (wild type) colonies.

III. Any colonies exhibiting a lighter color than wild type colonies are recovered from the master plate and regrown for-DNA sequencing, repeated color screening, and in vitro expression and characterization of drug resistance in the purified enzyme.

While the foregoing specification teaches the principles of the present invention, with examples provided for the purpose of illustration, it will be understood that the practice of the invention encompasses all of the

What is claimed is:

1. A color screen assay for inhibitor-resistant HIV protease mutants, comprising the steps of:
 (a) plating out an *E.coli* recipient strain transformed with a library of mutagenized, full-length HIV protease sequences in pPrBG1, said pPrBG1 comprising DNA coding for mutagenized HIV protease coordinately expressed with DNA coding for beta-galactosidase containing a substrate site cleavable by HIV protease, to give colonies on a master plate:
 (b) lifting said colonies onto nitrocellulose filters, to give colony lifts:
 (c) treating the colony lifts with one or more inhibitors of HIV protease, to give treated colony lifts;
 (d) incubating the treated colony lifts in induction medium, said induction medium comprising suitable growth media and a color-producing substrate for the beta-galactosidase containing a substrate site cleavable by HIV protease, to give induced colony lifts; and
 (e) selecting those colonies from the master plate that correspond to the lighter colored colonies on the induced colony lifts:
 to give inhibitor-resistant HIV protease mutants.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
   ( A ) LENGTH: 33 base pairs
   ( B ) TYPE: Nucleic Acid
   ( C ) STRANDEDNESS: Single
   ( D ) TOPOLOGY: Linear ( i i ) MOLECULE TYPE: DNA ( i i i ) HYPOTHETICAL: NO ( x i ) SEQUENCE DESCRIPTION: SEQ ID NO:1:

TGAGGTGAGC TTTAACTTCC CTCAGATCAC TCT          33

( 2 ) INFORMATION FOR SEQ ID NO:2:

( i ) SEQUENCE CHARACTERISTICS:
   ( A ) LENGTH: 33 base pairs
   ( B ) TYPE: Nucleic Acid
   ( C ) STRANDEDNESS: Single
   ( D ) TOPOLOGY: Linear ( i i ) MOLECULE TYPE: DNA ( i i i ) HYPOTHETICAL: NO ( x i ) SEQUENCE DESCRIPTION: SEQ ID NO:2:

TCAAGAGTGA TCTGAGGGAA GTTAAAGCTC ACC          33

( 2 ) INFORMATION FOR SEQ ID NO:3:

( i ) SEQUENCE CHARACTERISTICS:
   ( A ) LENGTH: 17 base pairs
   ( B ) TYPE: Nucleic Acid
   ( C ) STRANDEDNESS: Single
   ( D ) TOPOLOGY: Linear ( i i ) MOLECULE TYPE: DNA Primer ( i i i ) HYPOTHETICAL: NO ( x i ) SEQUENCE DESCRIPTION: SEQ ID NO:3:

GCTTTGCCTG GTTTCCG          17

( 2 ) INFORMATION FOR SEQ ID NO:4:

( i ) SEQUENCE CHARACTERISTICS:
   ( A ) LENGTH: 30 base pairs
   ( B ) TYPE: Nucleic Acid
   ( C ) STRANDEDNESS: Single
   ( D ) TOPOLOGY: Linear ( i i ) MOLECULE TYPE: DNA Primer ( i i i ) HYPOTHETICAL: NO ( x i ) SEQUENCE DESCRIPTION: SEQ ID NO:4:

CGATCAAGCT TAAGCCGTAG ATAAACAGGC          30

( 2 ) INFORMATION FOR SEQ ID NO:5:

( i ) SEQUENCE CHARACTERISTICS:

( A ) LENGTH: 42 base pairs
( B ) TYPE: Nucleic Acid
( C ) STRANDEDNESS: Single
( D ) TOPOLOGY: Linear ( i i ) MOLECULE TYPE: DNA Primer ( i i i ) HYPOTHETICAL: NO ( x i ) SEQUENCE DESCRIPTION: SEQ ID NO:5:

ATCCTGGGTC TCGAGCTATT ATTTTTGACA CCAGACCAAC TG　　　　　　　　　42

( 2 ) INFORMATION FOR SEQ ID NO:6:

( i ) SEQUENCE CHARACTERISTICS:
( A ) LENGTH: 18 base pairs
( B ) TYPE: Nucleic Acid
( C ) STRANDEDNESS: Single
( D ) TOPOLOGY: Linear ( i i ) MOLECULE TYPE: DNA Primer ( i i i ) HYPOTHETICAL: NO ( x i ) SEQUENCE DESCRIPTION: SEQ ID NO:6:

TTTTCGCTCA TGTGAAGT　　　　　　　　　18

( 2 ) INFORMATION FOR SEQ ID NO:7:

( i ) SEQUENCE CHARACTERISTICS:
( A ) LENGTH: 19 base pairs
( B ) TYPE: Nucleic Acid
( C ) STRANDEDNESS: Single
( D ) TOPOLOGY: Linear ( i i ) MOLECULE TYPE: DNA Primer ( i i i ) HYPOTHETICAL: NO ( x i ) SEQUENCE DESCRIPTION: SEQ ID NO:7:

TGCGTTCTGA TTTAATCTG　　　　　　　　　19

( 2 ) INFORMATION FOR SEQ ID NO:8:

( i ) SEQUENCE CHARACTERISTICS:
( A ) LENGTH: 17 base pairs
( B ) TYPE: Nucleic Acid
( C ) STRANDEDNESS: Single
( D ) TOPOLOGY: Linear ( i i ) MOLECULE TYPE: DNA Probe ( i i i ) HYPOTHETICAL: NO ( x i ) SEQUENCE DESCRIPTION: SEQ ID NO:8:

GTTTCCACAT GGGGATT　　　　　　　　　17

( 2 ) INFORMATION FOR SEQ ID NO:9:

( i ) SEQUENCE CHARACTERISTICS:
( A ) LENGTH: 30 base pairs
( B ) TYPE: Nucleic Acid
( C ) STRANDEDNESS: Single
( D ) TOPOLOGY: Linear ( i i ) MOLECULE TYPE: DNA Primer ( i i i ) HYPOTHETICAL: NO ( x i ) SEQUENCE DESCRIPTION: SEQ ID NO:9:

AGGAGGAATT CGACATATGC CTCAGATCAC　　　　　　　　　30

( 2 ) INFORMATION FOR SEQ ID NO:10:

( i ) SEQUENCE CHARACTERISTICS:
    ( A ) LENGTH: 30 base pairs
    ( B ) TYPE: Nucleic Acid
    ( C ) STRANDEDNESS: Single
    ( D ) TOPOLOGY: Linear ( i i ) MOLECULE TYPE: DNA Primer ( i i i ) HYPOTHETICAL: NO ( x i ) SEQUENCE DESCRIPTION: SEQ ID NO:10:

| | | |
|---|---|---|
| CAGCCAAGCT TAGAAGTTCA GAGTGCAGCC | | 30 |

( 2 ) INFORMATION FOR SEQ ID NO:11:

( i ) SEQUENCE CHARACTERISTICS:
        ( A ) LENGTH: 17 base pairs
        ( B ) TYPE: Nucleic Acid
        ( C ) STRANDEDNESS: Single
        ( D ) TOPOLOGY: Linear     ( i i ) MOLECULE TYPE: DNA Primer     ( i i i ) HYPOTHETICAL: NO     ( x i ) SEQUENCE DESCRIPTION: SEQ ID NO:11:

TAATACGACT CACTATA             17

( 2 ) INFORMATION FOR SEQ ID NO:12:

( i ) SEQUENCE CHARACTERISTICS:
        ( A ) LENGTH: 17 base pairs
        ( B ) TYPE: Nucleic Acid
        ( C ) STRANDEDNESS: Single
        ( D ) TOPOLOGY: Linear     ( i i ) MOLECULE TYPE: DNA Probe     ( i i i ) HYPOTHETICAL: NO     ( x i ) SEQUENCE DESCRIPTION: SEQ ID NO:12:

ATTTAGGTGA CACTATA             17

( 2 ) INFORMATION FOR SEQ ID NO:13:

( i ) SEQUENCE CHARACTERISTICS:
        ( A ) LENGTH: 339 base pairs
        ( B ) TYPE: Nucleic Acid
        ( C ) STRANDEDNESS: Single
        ( D ) TOPOLOGY: Linear     ( i i ) MOLECULE TYPE: Coding Sequence     ( i i i ) HYPOTHETICAL: NO     ( v i ) IMMEDIATE SOURCE: Protease Gene From NY5 Strain of HIV-1

( x i ) SEQUENCE DESCRIPTION: SEQ ID NO:13:

| | | | | | |
|---|---|---|---|---|---|
| CGATAATGTA | TGGATTAAAT | AAGGAGGAAT | AAGACATATG | CCTCAGATCA | 50 |
| CTCTGTGGCA | GCGGCCGCTG | GTTACTATCA | AAATCGGTGG | CCAGCTGAAA | 100 |
| GAAGCTCTTC | TAGACACTGG | TGCTGACGAC | ACTGTTCTCG | AGGAAATGAA | 150 |
| CCTGCCCGGG | CGTTGGAAAC | CTAAAATGAT | CGGTGGTATC | GGTGGTTTCA | 200 |
| TCAAAGTTCG | TCAGTATGAT | CAGATCCTGA | TCGAGATCTG | CGGTCATAAA | 250 |
| GCTATCGGTA | CCGTTCTGGT | TGGTCCTACT | CCTGTTAACA | TCATCGGTCG | 300 |
| TAACCTGCTG | ACCCAGATCG | GCTGCACTCT | GAACTTCTA | | 339 |

( 2 ) INFORMATION FOR SEQ ID NO:14:

(i) SEQUENCE CHARACTERISTICS:
  (A) LENGTH: 12 amino acids
  (B) TYPE: amino acid
  (C) TOPOLOGY: Linear (ii) MOLECULE TYPE:
  (A) DESCRIPTION: peptide (iii) HYPOTHETICAL: NO (iv) ANTI-SENSE: NO (v) FRAGMENT TYPE: internal fragment (xi) SEQUENCE DESCRIPTION: SEQ ID NO:14:

Glu Val Ser Phe Asn Phe Pro Gln Ile Thr Leu Glu
              5                           10

(2) INFORMATION FOR SEQ ID NO:15:

(i) SEQUENCE CHARACTERISTICS:
    (A) LENGTH: 8 amino acids
    (B) TYPE: amino acid
    (C) TOPOLOGY: Linear (ii) MOLECULE TYPE:
    (A) DESCRIPTION: peptide (iii) HYPOTHETICAL: NO (iv) ANTI-SENSE: NO (v) FRAGMENT TYPE: internal fragment (xi) SEQUENCE DESCRIPTION: SEQ ID NO:15:

Ser Gln Asn Tyr Pro Ile Val Gln
              5

(2) INFORMATION FOR SEQ ID NO:16:

(i) SEQUENCE CHARACTERISTICS:
    (A) LENGTH: 8 amino acids
    (B) TYPE: amino acid
    (C) TOPOLOGY: Linear (ii) MOLECULE TYPE:
    (A) DESCRIPTION: peptide (iii) HYPOTHETICAL: NO (iv) ANTI-SENSE: NO (v) FRAGMENT TYPE: internal fragment (xi) SEQUENCE DESCRIPTION: SEQ ID NO:16:

Ala Arg Val Leu Ala Glu Ala Met
              5

(2) INFORMATION FOR SEQ ID NO:17:

(i) SEQUENCE CHARACTERISTICS:
    (A) LENGTH: 8 amino acids
    (B) TYPE: amino acid
    (C) TOPOLOGY: Linear (ii) MOLECULE TYPE:
    (A) DESCRIPTION: peptide (iii) HYPOTHETICAL: NO (iv) ANTI-SENSE: NO (v) FRAGMENT TYPE: internal fragment (xi) SEQUENCE DESCRIPTION: SEQ ID NO:17:

Ala Thr Ile Met Met Gln Arg Gly
                    5

(2) INFORMATION FOR SEQ ID NO:18:

(i) SEQUENCE CHARACTERISTICS:
        (A) LENGTH: 8 amino acids
        (B) TYPE: amino acid
        (C) TOPOLOGY: Linear     (ii) MOLECULE TYPE:
        (A) DESCRIPTION: peptide     (iii) HYPOTHETICAL: NO     (iv) ANTI-SENSE: NO     (v) FRAGMENT TYPE: internal fragment     (xi) SEQUENCE DESCRIPTION: SEQ ID NO:18:

Pro Gly Asn Phe Leu Gln Ser Arg
                    5

(2) INFORMATION FOR SEQ ID NO:19:

(i) SEQUENCE CHARACTERISTICS:
        (A) LENGTH: 8 amino acids
        (B) TYPE: amino acid
        (C) TOPOLOGY: Linear     (ii) MOLECULE TYPE:
        (A) DESCRIPTION: peptide     (iii) HYPOTHETICAL: NO     (iv) ANTI-SENSE: NO     (v) FRAGMENT TYPE: internal fragment     (xi) SEQUENCE DESCRIPTION: SEQ ID NO:19:

Ser Phe Asn Phe Pro Gln Ile Thr
                    5

(2) INFORMATION FOR SEQ ID NO:20:

(i) SEQUENCE CHARACTERISTICS:
        (A) LENGTH: 8 amino acids
        (B) TYPE: amino acid
        (C) TOPOLOGY: Linear     (ii) MOLECULE TYPE:
        (A) DESCRIPTION: peptide     (iii) HYPOTHETICAL: NO     (iv) ANTI-SENSE: NO     (v) FRAGMENT TYPE: internal fragment     (xi) SEQUENCE DESCRIPTION: SEQ ID NO:20:

Thr Leu Asn Phe Pro Ile Ser Pro
                    5

(2) INFORMATION FOR SEQ ID NO:21:

(i) SEQUENCE CHARACTERISTICS:
        (A) LENGTH: 8 amino acids
        (B) TYPE: amino acid
        (C) TOPOLOGY: Linear     (ii) MOLECULE TYPE:
        (A) DESCRIPTION: peptide     (iii) HYPOTHETICAL: NO ( i v ) ANTI-SENSE: NO ( v ) FRAGMENT TYPE: internal fragment ( x i ) SEQUENCE DESCRIPTION: SEQ ID NO:21:

Ala Glu Thr Phe Tyr Val Asp Gly
                    5

( 2 ) INFORMATION FOR SEQ ID NO:22:

( i ) SEQUENCE CHARACTERISTICS:
        ( A ) LENGTH: 8 amino acids
        ( B ) TYPE: amino acid
        ( C ) TOPOLOGY: Linear     ( i i ) MOLECULE TYPE:
        ( A ) DESCRIPTION: peptide     ( i i i ) HYPOTHETICAL: NO     ( i v ) ANTI-SENSE: NO     ( v ) FRAGMENT TYPE: internal fragment     ( x i ) SEQUENCE DESCRIPTION: SEQ ID NO:22:

Arg Lys Ile Leu Phe Leu Asp Gly
                    5

( 2 ) INFORMATION FOR SEQ ID NO:23:

( i ) SEQUENCE CHARACTERISTICS:
        ( A ) LENGTH: 8 amino acids
        ( B ) TYPE: amino acid
        ( C ) TOPOLOGY: Linear     ( i i ) MOLECULE TYPE:
        ( A ) DESCRIPTION: peptide     ( i i i ) HYPOTHETICAL: NO     ( i v ) ANTI-SENSE: NO     ( v ) FRAGMENT TYPE: internal fragment     ( x i ) SEQUENCE DESCRIPTION: SEQ ID NO:23:

Gln Ile Thr Leu Trp Gln Arg Pro
                    5

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( C ) TOPOLOGY: Linear     ( i i ) MOLECULE TYPE:
        ( A ) DESCRIPTION: peptide     ( i i i ) HYPOTHETICAL: NO     ( i v ) ANTI-SENSE: NO     ( v ) FRAGMENT TYPE: internal fragment     ( x i ) SEQUENCE DESCRIPTION: SEQ ID NO:24:

Asp Thr Val Leu Glu Glu Met Ser
                    5

( 2 ) INFORMATION FOR SEQ ID NO:25:

( i ) SEQUENCE CHARACTERISTICS:
        ( A ) LENGTH: 8 amino acids
        ( B ) TYPE: amino acid (C) TOPOLOGY: Linear (ii) MOLECULE TYPE:
(A) DESCRIPTION: peptide (iii) HYPOTHETICAL: NO (iv) ANTI-SENSE: NO (v) FRAGMENT TYPE: internal fragment (xi) SEQUENCE DESCRIPTION: SEQ ID NO:25:

Asp Gln Ile Leu Ile Glu Ile Cys
            5